United States Patent [19]

Scher

[11] 4,140,516
[45] Feb. 20, 1979

[54] ENCAPSULATION PROCESS EMPLOYING PHASE TRANSFER CATALYSTS

[75] Inventor: Herbert B. Scher, Moraga, Calif.

[73] Assignee: Stauffer Chemical Company, Westport, Conn.

[21] Appl. No.: 801,932

[22] Filed: May 31, 1977

[51] Int. Cl.² .................. A01N 9/00; A01N 17/00; B01J 13/02
[52] U.S. Cl. .................................. 71/88; 71/64 F; 71/100; 71/118; 71/DIG. 1; 252/316; 424/19; 424/32
[58] Field of Search ................. 252/316; 71/64 F, 88, 71/100; 424/19, 32

[56] References Cited

U.S. PATENT DOCUMENTS

| | | | |
|---|---|---|---|
| 1,112,755 | 10/1914 | Bergstrom | 424/10 |
| 3,576,760 | 4/1971 | Gould et al. | 424/32 X |
| 3,577,515 | 5/1971 | Vandegaer | 252/316 X |
| 3,660,304 | 5/1972 | Matsukawa | 252/316 |
| 3,701,759 | 10/1972 | Lee et al. | 424/276 X |
| 3,726,804 | 4/1973 | Matsukawa et al. | 252/316 |
| 4,046,741 | 9/1977 | Scher | 252/316 X |

*Primary Examiner*—Richard D. Lovering
*Attorney, Agent, or Firm*—Harry A. Pacini

[57] ABSTRACT

An improved encapsulation process to prepare encapsulated water-immiscible material employing an organic polyisocyanate intermediate to form discrete polyurea capsule enclosures around a water-immiscible material dispersed in an aqueous continuous phase said improvement comprising the addition of a catalytic amount of a phase transfer catalyst.

46 Claims, No Drawings

ENCAPSULATION PROCESS EMPLOYING PHASE TRANSFER CATALYSTS

BACKGROUND OF THE INVENTION

This invention relates to encapsulation and particularly to the production of small or minute capsules constituted by a skin or a thin wall of organic composition enclosing a body of material such as a liquid. The process of this invention is directed to the production of such capsules which may be produced to a predetermined size, and in a convenient and rapid method by chemical reaction in situ, wherein a suspension or a collection of discrete spheres or capsular spheroids is formed in a body of liquid which then may be readily separated or retained and used in said liquid.

Capsules of this nature and description have a variety of uses, such as for containing dyes, inks, chemical reagents, pharmaceuticals, flavoring materials, fungicides, bactericides, pesticides, such as herbicides, insecticides and the like, which substances can be dissolved, suspended or otherwise dispersed in or as the material to be enclosed by the capsule. The material to be encapsulated can be employed in the initial dispersion at a temperature above its melting point, or dissolved or dispersed in suitable water-immiscible organic solvent. The nature of the water-immiscible material to be encapsulated can be organic or inorganic in origin. Once encapsulated, the liquid or other form is preserved until it is released by some means or instrumentality that breaks, crushes, melts, dissolves or otherwise removes the capsule skin, or until release by diffusion is effected under suitable conditions. An important specific aspect of this invention, together with other features and advantages contemplated by the invention, is the procedure for polymerization involving the reaction between polyisocyanate monomers, to produce a capsular skin of polyurea.

DESCRIPTION OF THE PRIOR ART

A variety of techniques have been heretofore used or described for encapsulation purposes. Among these is the method, wherein the enclosing film is deposited by condensation and other procedures which involve polymerizing a substance contained in droplets or in a surrounding continuous liquid phase, so as to deposit the resulting polymer at the surface of such droplets. Another method involves the shooting of droplets through a falling film of liquid capsule-wall material which then solidifies around the individual droplets. Various methods of encapsulation by interfacial condensation between direct-acting, complimentary reactants are known. Within these methods are reactions for producing various types of polymers as the capsule walls. Many of such reactions to produce the coating substance occur between an amine which must be of at least difunctional character and a second reactant intermediate of acid or, more accurately, acid-derived nature, which for producing a polyamide is a difunctional or polyfunctional acid chloride. The amines chiefly used or proposed in these methods are typified by ethylene diamine or the like, having at least two primary amino groups.

For many processes of encapsulation, there is a final requirement of separation of the encapsulated materials from the forming media. During the separation process, the capsule wall material is subjected to great mechanical stress. For this reason, the highly desirable thin skin or cell wall is greatly restricted in the prior art methods. A particular object of the present invention is to provide a new and improved encapsulation process which is rapid and effective and which avoids the necessity of separation of the encapsulated material. A special advantage, therefore, is the permissible formation of extremely thin skin or cellular wall in conjunction with the capsules.

Interfacial polymerization generally involves bringing together two immiscible heterogeneous liquids, e.g., water and organic solvent, respectively, containing complimentary, direct-acting, organic intermediates that will react with each other to establish a solid polycondensate. Such polycondensates, such as a polyamide, polyester, polyurethane, polyurea, or like substances, can be formed from resin intermediates or monomers. It has also been proposed to spray droplets of organic solvent containing a diacid chloride into an aqueous liquid containing, for instance, ethylene glycol with the object of encapsulating the organic liquid or oil in polyester capsules. These efforts have fallen short of a practical value in various respects. For example, special apparatus is required for this technique. Further, various experiments have indicated the difficulty in establishing the desired capsules in discrete form whereby coalescense of the partially formed capsules into a heterogeneous mass of materials lacking distinct capsule formation will result. Control of capsule size or uniformity is troublesome in the prior art method. The processes appear limited in types of reactions and products involved.

One particular method of encapsulation by interfacial polycondensation is disclosed in U.S. Pat. No. 3,577,515, issued May 4, 1971. This patent describes a continuous or batch method which requires a first reactant and a second reactant complimentary to the first reactant with each reactant in separate phases, such that the first and second reactant react at the interface between the droplets to form encapsulated droplets. As will become apparent hereinafter, the instant invention eliminates the necessity for a second reactant wherein it has been found that a polyurea type encapsulation body can be formed with great ease and provides special advantages.

Reference is made to French Pat. No. 1,415,039 which discloses a multifacit technology employing various polymer systems for encapsulation, however, with no description of the instant invention. That is, there is no teaching of the use of phase transfer catalysts in any encapsulation process.

Reference is made to Belgian Pat. No. 796,746, assigned to Stauffer Chemical Company, published Sept. 14, 1973. The aforementioned patent describes a method for encapsulating various water-immiscible materials employing an organic isocyanate intermediate to form a polyurea capsule enclosure around a water-immiscible material dispersed in an aqueous continuous phase.

SUMMARY OF THE INVENTION

This invention relates to encapsulation and particularly to the method of production of small of minute capsules constituted by a skin or a thin wall of organic polymer composition enclosing a water-immiscible material, such as an organic liquid. More particularly, this invention relates to an improved method for production of discrete polyurea microcapsules containing various core materials by the addition of a phase transfer catalyst to the organic phase.

In contradistinction to the prior art and in accordance with the preferred practice of the present invention, it has been discovered that effective encapsulation by interfacial polymerization of an organic isocyanate intermediate can be effectively enhanced by the addition of a phase transfer catalyst in the process which utilizes two substantially heterogeneous immiscible liquids, one termed an aqueous phase and the other termed an organic phase, and which comprises establishing a physical dispersion of the organic phase in the aqueous phase, said organic phase containing the organic isocyanate intermediate for the polyurea capsule skin or enclosure. The interfacial polymerization of the present invention to form the capsular wall involves hydrolysis of an isocyanate monomer in the presence of a catalytic amount of phase transfer catalyst to form an amine which in turn reacts with another isocyanate monomer to form the polyurea enclosure. The addition of no other reactant is required once the dispersion establishing droplets of the organic phase within a continuous liquid phase, i.e., aqueous phase, has been accomplished. Thereafter, and preferably with moderate agitation of the dispersion, the formation of the polyurea capsule skin or enclosure around the dispersed organic droplets is enhanced by the catalytic action of an agent known as a phase transfer catalyst capable of increasing the rate of isocyanate hydrolysis, thereby effecting the desired condensation reaction at the interface between the organic droplets and the continuous phase without external heating of the dispersion.

In this fashion, fully satisfactory, discrete capsules are formed having a skin consisting of the polyurea produced by the reaction and containing the encapsulated water-immiscible material. Within the process of the invention the reaction which forms the skin or enclosure for the capsule generally is complete, such that essentially no unreacted polyisocyanate remains. It is not necessary to separate the capsules for desired utilization, i.e., the encapsulated material may be directly usable, depending of course upon the intended utilization. However, such separation prior to utilization may be carried out by any of the normal separation processes involving, for example, settling, filtration or skimming of the collected capsules, washing and, if desired, drying. The product from the process of this invention is particularly suitable for direct agricultural pesticidal applications, additional agents can be added such as thickeners, biocides, surfactants and dispersants to improve storage stability and ease of application. The initial dispersion of the organic phase in the aqueous phase may be assisted with an appropriate emulsifying or dispersing agent and the control of the size and uniformity of the ultimate capsules is readily effected by any convenient method to disperse one liquid into another.

DETAILED DESCRIPTION OF THE INVENTION

In all cases, within the practice of the present invention, the effective procedure involves first, producing, as by simple agitation, a solution of water, a suitable surfactant and protective colloid. These three ingredients comprise the aqueous phase or continuous phase of the process. The aqueous or continuous phase is essentially free of any components that will react with the material therein or any of such groups of materials. The surfactant and protective colloid in the aqueous phase do not enter into the polycondensation reaction by which the capsule wall is formed.

By way of further exemplification, the surfactants in the aqueous or continuous phase can be described as nonionic or anionic surfactants in the HLB (hydrophile-lipophile balance) range from about 12 to about 16. There are many surfactants which satisfy this HLB range requirement. Among the acceptable surfactants are the compounds known as sodium isopropyl naphthalene sulfonate, polyoxyethylenesorbitol oleate laurate, ethoxylated nonylphenols, however, the preferred surfactant is of the class polyethylene glycol ethers of linear alcohols. Whereas the surfactant is described herein as placed in the aqueous phase, it can also be placed in the organic phase. Without specific reference to the phase in which the surfactant is placed, there will be a partitioning and distribution of the surfactant between each phase upon the mixing of the phases depending upon the relative solubility therein. Use of a surfactant may be omitted provided that a sufficiently high shear rate is employed to form the dispersion. In the preferred embodiment of this invention a surfactant is employed. The range of surfactant concentration found most acceptable in this system is from about 0.01 percent to about 3.0 percent by weight based on the aqueous phase. Higher concentration of surfactant may be used without increased ease of dispersibility.

Also present in the aqueous or continuous phase is a protective colloid which can be selected from a wide range of such materials. The usable protective colloids can be exemplified by the following: Polyacrylates, methyl cellulose, polyvinyl alcohol, polyacrylamide and poly(methylvinyl ether/maleic anhydride). The amount of colloid employed will depend upon various factors such as molecular weight, type and effectiveness within the media, compatability and the like. It has been found that the protective colloid can be added to the aqueous phase prior to addition of the organic phase to the aqueous phase. Alternatively, the protective colloid can be added to the system following the addition of the organic phase or following the dispersion thereof. As another alternative, the protective colloid can be added partially prior to addition of the organic phase and partially after the dispersion step. Generally, from about 0.1 percent to about 5.0 percent by weight based on the aqueous phase is used.

A second phase, known as the organic phase, comprises the material to be encapsulated, a polyisocyanate and phase transfer catalyst. The material to be encapsulated can be used in a concentrated form or in a solution of a water-immiscible solvent. The material to be encapsulated can be used as the solvent for the polyisocyanate and phase transfer catalyst. However, to achieve a desired concentration of active material in the final product, a water-immiscible organic solvent can be used to dissolve the material to be encapsulated, polyisocyanate and phase transfer catalyst. The material to be encapsulated and the polyisocyanate are added simultaneously to the aqueous phase. Whereas, the material to be encapsulated and the polyisocyanate may be added separately with slow agitation in the reactor for a time sufficient to cause a homogeneous organic solution, the preferred method of simultaneous addition of the components of the organic phase is in a pre-mixed state. That is, the material to be encapsulated and the polyisocyanate are pre-mixed to obtain a homogeneous phase before addition to and mixing with the aqueous phase. The amount of the organic phase may vary from about 1 percent to about 75 percent by volume of the aqueous phase present in the reaction vessel. The concentrations in the lower end of the range are relatively undesirable since they result in a very dilute suspension of capsules. The preferred amount of organic phase is about 25 percent to about 50 percent by volume.

The nature of the organic polyisocyanate determines the release properties of the capsule formed by this process. The polyisocyanates also determine the structural physical strength of the capsular wall. The organic polyisocyanates employed in this process include those members of the aromatic polyisocyanate class which includes the aromatic diisocyanates, the aliphatic diisocyanates and the isocyanate pre-polymers. Representative of the aromatic and aliphatic diisocyanates and other polyisocyanates are the following:

1-Chloro-2,4-phenylene diisocyanate
m-Phenylene diisocyanate
p-Phenylene diisocyanate
4,4'-Methylenebis (phenyl isocyanate)
2,4-Tolylene diisocyanate
Tolylene diisocyanate (60% 2,4-isomer, 40% 2,6-isomer)
2,6-Tolylene diisocyanate
3,3'-Dimethyl-4,4'-biphenylene diisocyanate
4,4'-Methylenebis (2-methylphenyl isocyanate)
3,3'-Dimethoxy-4,4'-biphenylene diisocyanate
2,2',5,5'-Tetramethyl-4,4'-biphenylene diisocyanate
80% 2,4- and 20% 2,6-isomer of tolylene diisocyanate
Polymethylene polyphenylisocyanate (PAPI)
Hexamethylene diisocyanate (HMDI)

It is highly desirable to use combinations of the above-mentioned organic polyisocyanates. Such combinations as, for example, polymethylene polyphenylisocyanate and tolylene diisocyanate, containing 80% 2,4- and 20% 2,6-isomers, produce excellent capsular enclosures with exceptional controlled release properties.

The use of a phase transfer catalyst allows the use of aliphatic isocyanates, such as hexamethylene diisocyanate for capsule wall formation at 25° C. or ambient temperatures. Without a phase transfer catalyst the aliphatic diisocyanates react too slowly even at elevated temperatures. This permits favorable blending of aliphatic and aromatic isocyanates and thereby modify the permeability of the microcapsule wall.

The amount of organic polyisocyanate used in the process will determine the wall content of the capsules formed therein. Generally, based on the organic phase, there will be greater than about 2 percent by weight organic polyisocyanate present. However, this is by no means limiting and a greater amount can be used that is approaching about 100 percent. Clearly, 100 percent would not be entirely desirable since this would result in a product with no encapsulated material. The preferred range is from about 2.0 percent to about 75.0 percent by weight of organic polyisocyanate, thereby forming an encapsulated product having a corresponding wall content, i.e., about 2.0 percent to about 75.0 percent. More particularly, the preferred range is from about 5.0 percent to about 50.0 percent wall content.

In accordance with preferred practice of the present invention, the following general steps comprise the process which utilizes the two substantially immiscible phases described above. In essence, the process comprises establishing a physical dispersion of the organic phase (containing a catalytic amount of phase transfer catalyst) in the aqueous or continuous phase, such dispersion thereby establishing droplets of desired size in the aqueous phase. Thereafter, by adjusting the pH of the resulting mixture, the desired condensation reaction is effected at the interfaces between the droplets and the continuous phase. Certain variations in the sequence of steps between adjustment of the pH and addition of a phase transfer catalyst will be apparent in the following discussion and examples.

The temperatures of the two-phase mixture, that is, the dispersion of the organic phase in the aqueous phase, does not require external heating. The temperature range for the condensation reaction within the present invention in the presence of the phase transfer catalyst is between about 20° C. to about 25° C. Whereas, heating is required to initiate the reaction of this process without the phase transfer catalyst no heating is required when the phase transfer catalyst is present. Ambient temperature conditions are usable in this process. The rate of reaction is extremely rapid upon increasing the pH of the dispersion to about pH 8 to about pH 12. In an alternative procedure, the adjustment of the pH is performed after the dispersion is accomplished and the pH is maintained within the limits to be discussed below.

Within the improvement of the present invention, it has been found that a catalyst, known as a phase transfer catalyst, is capable of increasing the rate of isocyanate hydrolysis. Addition of the phase transfer catalyst is made to the organic phase prior to the initiation of the desired condensation reaction at the interface to form the capsules. There is no need to increase the temperature of the system when a phase transfer catalyst is employed as described herein. The catalyst in such a procedure is added preferably to the organic phase and is added to the system at the time of mixing of the aqueous and organic phases. Various catalysts of the phase transfer type have been found acceptable, their selection will depend upon factors easily determinable by one skilled in the art.

The term "phase transfer catalyst" is used herein to represent any catalyst which can effectively facilitate the transfer of ions or other reactive or functional chemical species or groups across the phase interface between one distinct liquid phase and a second distinct liquid phase, as in a heterogeneous system. In the majority of cases, one of the reactants is located in an aqueous phase and the other reactant in an organic phase.

Certain organic quaternary salts of Group VA of the Periodic Table of the Elements have been found effective as "phase transfer catalyst" useful in the rapid formation of microcapsules according to the present invention.

Examples of such catalysts are quaternary salts having the formula

$(R_3 R_4 R_5 R_6 M)^+ X^-$ , wherein $R_3$, $R_4$, $R_5$ and $R_6$ are hydrocarbon radicals having a total sum of 18 to 70 carbon atoms selected independently from the group consisting of alkyl, alkenyl, aryl, alkaryl, aralkyl and cycloalkyl radicals; M is a pentavalent ion selected from the group consisting of nitrogen, phosphorus, arsenic, antimony, and bismuth, preferably nitrogen or phosphorus; and X is an anion which will dissociate from the cation in an aqueous environment, preferably a halide ion or a hydroxyl ion, most preferably chloride or bromide. The number of carbon atoms in the hydrocarbon substituents may vary considerably so as to contain from 1 to about 25 or more carbon atoms in each instance.

As used in the description of $R_3$, $R_4$, $R_5$, and $R_6$ above:

The term "alkyl" refers to a monovalent straight or branched chain saturated aliphatic hydrocarbon group of 1 to 25 carbon atoms, inclusive, e.g., methyl, ethyl, propyl, i-propyl, n-butyl, s-butyl, t-butyl, n-octyl, 2-methyloctyl, decyl, 6-methylundecyl, dodecyl, and the like;

the term "alkenyl" refers to a monovalent straight or branched chain aliphatic hydrocarbon of 2 to 25 carbon atoms, inclusive, and containing at least one double bond, e.g., allyl, butenyl, butadienyl, and the like;

the term "aryl" refers to a monovalent monocyclic or bicyclic aromatic hydrocarbon group, i.e., phenyl and naphthyl;

the term "alkaryl" refers to an aryl group as defined above, in which at least one hydrogen atom is substituted by an alkyl group as defined above, e.g., tolyl, xylyl, mesityl, ethylphenyl, and the like;

the term "aralkyl" refers to an alkyl group as defined above, in which a hydrogen atom is substituted by an aryl or alkaryl group as defined above, e.g., benzyl, phenethyl, methylbenzyl, naphthylmethyl, and the like; and the term "cycloalkyl" refers to a monovalent cyclical saturated hydrocarbon group of 4 to 8 carbon atoms, inclusive, i.e., cyclobutyl, cyclopentyl, cyclohexyl, cycloheptyl, and cyclooctyl.

Mixtures of such quaternary salts may be likewise utilized in the practice of this invention. Double or multifunctional quaternary salts in which the general formula $(R_3R_4R_5R_6M)^+X^-$ is repeated a plurality of times with the same or different substituent combinations, can also be utilized effectively.

The preferred phase transfer catalysts are tetra-n-butyl phosphonium chloride, tri-n-butyl n-cetyl phosphonium bromide, hexadecyl tributyl phosphonium bromide, benzyl triethyl ammonium chloride, benzyl triethyl ammonium bromide, trioctyl ethyl ammonium bromide, tetraheptyl ammonium iodide, triphenyl decyl phosphonium iodide, tribenzyl decyl arsonium chloride, tetranonylammonium hydroxide, tricaprylyl methyl ammonium chloride, and dimethyl dicoco ammonium chloride. The latter two catalysts are manufactured by General Mills Co., Chemical Division, Kankakee, Illinois, and are alternatively designated by the names "Aliquat 336" and "Aliquat 221", respectively.

The term "catalytic amount" is used herein to represent any amount of phase transfer catalyst (quaternary salt) which will enhance the progress of the reaction. The amount of catalyst normally used will range from about 0.05 weight percent to about 5.0 weight percent based on the organic phase, preferably from about 0.2 weight percent to about 2.0 weight percent based on the organic phase.

The terms catalytic activity and catalysis as they are here used are intended to mean that a finite increase in the extent to which, or the rate at which, the reactants in the several phases react with each other is caused to occur by the presence in the system of the quaternary salt. Thus, there may or may not be an economic advantage to conducting the catalysis in the case of a particular reaction, but, as will be hereinafter shown in microencapsulation technology involving heterogeneous ionic reactions, a striking improvement in reactivity is realized which makes the heterogeneous or multiphase environment a much more attractive route by which to produce microcapsules than any method heretofore available.

It is satisfactory to prepare the aqueous phase as described above. While stirring the aqueous phase, the organic phase is added, preferably in a pre-mixed state. Upon addition of the organic phase to the aqueous phase, a suitable dispersing means to disperse one liquid into the other is employed. Any high shear device can be used conveniently to obtain the desired droplet size within the range of from about 0.5 microns to about 4,000 microns. The actual range will depend upon the desired end use. As an example, the preferred range for most pesticidal applications is from about 1 micron to about 100 microns. The actual range will depend upon the desired end use. The instant process is applicable to preparing widely varied but uniform sized capsules. Once the proper droplet size is obtained, the dispersion means employed to establish the desired droplet size is discontinued. Only mild agitation is required for the balance of the process.

The process of the instant invention is capable of satisfactory performance and production of encapsulated material with easy adjustment of pH to facilitate the reaction. At a low pH value (about 2 to about 5), the rate of wall formation is slow even with a phase transfer catalyst present. This is advantageous to allow time for dispersion of the organic phase. However, satisfactory dispersion can take place in the pH range of from about 2 to about 8. When properly dispersed to the desired particle size, the pH is raised to about pH 8 to about pH 12 preferably pH 10, at which value the wall forming reaction for the microcapsules takes place rapidly. In an alternative procedure, the encapsulation process can be achieved by initially adjusting the pH of the aqueous phase to about 5 to about 10, without further pH adjustment after dispersion. In most instances the reaction is about two-thirds complete in the initial 5 minutes after raising the pH value to about 10 at ambient temperature or about 25° C. This is to be directly compared to the situation occurring in the absence of the phase transfer catalyst. Without a phase transfer catalyst present only about one-half completion is achieved in 60 minutes at 25° C. depending upon the type of diisocyanate and material to be encapsulated.

The encapsulation process will proceed most satisfactory at a pH value of between about 8 to about 14, more preferably between about 8 to about 12. The desirability of any adjustment of pH to a particular value will depend upon the nature of the systems components, such as surfactant, colloid, catalyst, temperature, material to be encapsulated and the like. The pH is adjusted after dispersion and maintained at that value for the remainder of the condensation reaction. The adjustment of the pH takes place in the aqueous phase following the dispersion therein of the organic phase. The adjustment and maintenance of a particular pH throughout the reaction can be accomplished with various water soluble bases or acids nonreactive with the polyisocyanate intermediate. Preferably, sodium hydroxide (10% solution), potassium hydroxide, hydrochloric acid and the like can be used.

The desired condensation reaction at the interface between the droplets and the continuous phase occurs extremely rapidly in the presence of a phase transfer catalyst. The majority of the reaction is complete within the first five to ten minutes of reaction time. There is no need to continue the reaction conditions for an extended period of time to insure completion of the reaction. Under properly adjusted pH conditions and with a phase transfer catalyst, the reaction time is shortened. At the end of this short time, the formation of a capsule wall has been completed, thereby encapsulating the organic material within the skin of a polycondensate, and there exists a usable encapsulated product. A specific feature of the present invention, which is highly desirable, resides in the fact that for certain intended applications, no further separation or handling of the encapsulated material is required, i.e., the product is directly usable. The encapsulated material can be used for various direct applications at this point or indirectly by incorporating the material into other products.

The thickness or chemical composition of the capsule-wall can be selected or controlled in various ways. For example, these properties can be affected by control of the reaction condition, by chemical selection, especially in the creation of cross-linkage which is determined by the functionality of the polyisocyanate in accordance with the technology. The thickness of the capsule skin can also be altered by varying the amounts of reactants within the organic phase. One convenient mode of controlling the size of the capsule is adjustment of the speed of agitation, that is, in bringing about the original dispersion of the organic phase, smaller capsules can be obtained with higher speeds of agitation resulting in a greater shearing force.

Tests have indicated that capsules produced in accordance with the present invention can be utilized in the same manner as products of other encapsulation procedures. Thus, for example, encapsulated herbicides or insecticides can be embodied in dispersions for application purposes, for controlled release of the encapsulated material at the desired locality. Special utility is noted for the encapsulation of various volatile or unstable insecticides and herbicides. By encapsulation, premature volatilization or other deterioration of the material is avoided; such encapsulation can also serve the purpose of retarding or delaying action to the time when desired. Controlled release of these materials is important for environmental protection and the proper effect on the organism to be controlled, as well as decreased toxicity on beneficial organisms.

The present invention may be practiced in a batch or batch-like form or in a continuous or continuous-like form. When the invention is practiced in a manner resembling a batch process, all the various liquids and various reactants will be brought together and various steps determined by the proper time sequence into a single body of liquid. The batch process may be altered by using the suitable reactors such that a continuous or continuous-like form of the encapsulation process is achieved.

Due to the extremely rapid rate of capsule wall formation in the presence of a phase transfer catalyst a continuous process is part of this invention. In the continuous form of the inventive process, continuous dispersion and agitation of the reacting phases may be practiced at a proper rate to continuously form a suitable dispersion of droplets in the aqueous phase and such that a continuously supplied portion of the dispersion of droplets in an aqueous phase is added to a reactor in which the pH can be adjusted to promote the interfacial condensation. Within the continuous system, the proper rate for reaction may be obtained by selecting the appropriate conditions. Both the batch and continuous aspects of the present invention are highly desirable, and choice there between will rest solely with the desired manufacturing conditions.

EXAMPLE I

Water (279g.), containing 2.0% of neutralized poly(methyl vinyl ether/maleic anhydride) protective colloid (Gantrez AN 119), 0.22% polyvinyl alcohol, protective colloid (Vinol 205) and 0.3% linear alcohol ethoxylate emulsifier (Tergitol 15-5-7) is placed into an open reactor vessel. The pH is adjusted to about 4.3 with sodium hydroxide solution. In a separate container 340g. of S-ethyl diisobutyl thiocarbamate (an herbicide), 14.2g. of N,N-diallyl dichloroacetamide (an herbicide antidote), 15.8g. polymethylene polyphenylisocyanate (PAPI), 12.9g. tolylene diisocyanate (TDI) and 2.3g. tricaprylyl methyl ammonium chloride (a phase transfer catalyst, also known as "Aliquat 336") are mixed together.

This mixture is then added to the reactor vessel and emulsified with a high shear stirrer. The resulting particle size is in the range of from about 5 microns ($\mu$) to about 40 microns ($\mu$). Only mild agitation is required for the remainder of the reaction. No heating is required. The pH of the resulting mixture is adjusted to about 10.0 with a 20% sodium hydroxide solution. At pH about 10.0 the microcapsule wall formation is about 93.2% complete in about two (2) minutes. Well formed, discrete microcapsules are observed under a microscope.

In contrast, conventional polyurea microcapsule formation as described, without the phase transfer catalyst, requires about 3 hours at 50° C.

EXAMPLE II

In a similar procedure as described in Example I, to 471.7g. of water containing 2.0% neutralized poly(methylvinyl ether/maleic anhydride) protective colloid (Gantrez AN 119) 0.22% polyvinyl alcohol protective colloid (Vinol 205) and 0.3% linear alcohol ethoxylate emulsifier (Tergitol 15-5-7) in an open vessel is added the mixture of 170G. S-ethyl diisobutylthiocarbamate (an herbicide), 7.1g. N,N-diallyl dichloroacetamide (an herbicide antidote), 7.9g. polymethylene polyphenylisocyanate (PAPI), 6.45g. hexamethylene diisocyanate (HMDI) and 1.29g. tricaprylyl methyl ammonium chloride. The particle size is established in the range of about 5$\mu$ to about 40$\mu$. The pH of the reaction mixture was adjusted to about 10.0 with sodium hydroxide solution. In about 2 minutes the formation of microcapsules in the dispersion is 50% complete. Continued stirring will increase the decimal degree of completion. The degree of completion is judged by sodium hydroxide consumption. Discrete well-formed particles are observed under a microscope.

EXAMPLE III

In a similar procedure as described in EXAMPLE I, to 1710g. of water containing 2.0% neutralized poly-(methyl vinyl ether/maleic anhydride) protective colloid (Gantrez AN 119), 0.22% polyvinyl alcohol protective colloid (Vinol 205) and 0.3 linear alcohol ethoxylate emulsifier (Tergitol 15-5-7) in an open vessel is added the mixture of 1700g. S-ethyl hexahydro -1H-azepine-1-carbothioate (an herbicide), 92.0g. polymethylene polyphenylisocyanate (PAPI), 46.0g. tolylene diisocyanate (TDI) and 11.0g. tricaprylyl methyl ammonium chloride (a phase transfer catalyst - "Aliquat 336"). The particle size is established as described above in the range from about 5$\mu$ to about 40$\mu$. The pH is initially adjusted to 4.5 then raised to about 10.0 where the capsule formation takes place. After stirring for about 20 minutes, discrete well-formed capsules are obtained in good yield.

EXAMPLE IV

In a similar procedure as described in EXAMPLE I, to 378g. of water containing 2.0% polyvinyl alcohol protective colloid (Vinol 205) and 0.3% linear alcohol ethoxylate emulsifier (Tergitol 15-5-7) in an open vessel is added the mixture of 317g. O,O-dimethyl O-p-nitrophenyl phosphorothioate (an herbicide), 19.3g. polymethylene polyphenylisocyanate (PAPI), 6.4g. tolylene diisocyanate (TDI) and 2.1g. tricaprylyl methyl ammonium chloride (Aliquat 336). Emulsification is carried out as previously described. At this point, the pH is about 5.8, the particle size is established at about $5\mu$ to about $40\mu$. Mild agitation is continued for one hour with the temperature at about 25° C. At the end of this time well-formed discrete microcapsules are obtained. To react any unwanted residual isocyanate 12.5g. of 28% ammonia solution is added. The final pH adjustment to about pH 7 is made with concentrated hydrochloric acid.

EXAMPLE V

In a similar procedure as described in EXAMPLE I, to 509g. of water containing 2.0% polyvinyl alcohol protective colloid (Vinol 205) and 0.3% linear alcohol ethoxylate emulsifier (Tergitol 15-5-7) is added 165g. S-ethyl diisobutyl thiocarbamate (an herbicide), 7.3g. polymethylene polyphenylisocyanate, 6.0g. tolylene diisocyanate and 1.0g. tri-n-butyl n-cetyl phosphonium bromide (a phase transfer catalyst). There is no initial pH adjustment. Emulsification is carried out as previously described. The particle size is established at about $5\mu$ to about $40\mu$. At this point the pH is adjusted to about 10.0 with sodium hydroxide solution. In about six (6) minutes the formation of microcapsules is about 56.5% complete. Stirring is continued until the desired degree of completion is achieved as determined by sodium hydroxide consumption.

Discrete well-formed microcapsules are observed with a microscope.

As previously mentioned and illustrated by the examples herein, the improved process for encapsulation of the instant invention employing a phase transfer catalyst provides capsules capable of controlling release of encapsulated organic material. Representative and especially of importance are the process and capsules comprising as a constituent in the organic phase herbicides of the class thiocarbamate such as S-ethyl diisobutylthiocarbamate; S-ethyl dipropylthiocarbamate; S-ethyl hexahydro-1-H-azepine-1-carbothioate; S-propyl hexahydro-1-H-azepine-1-carbothioate; S-propyl dipropylthiocarbamate; S-ethyl ethylcyclohexyl thiocarbamate; S-4-chlorobenzyl diethyl thiocarbamate; S-propyl butylethyl thiocarbamate; organo phosphorus insecticides of the class organo phosphoro and phosphorothioates and dithioates such as O-ethyl S-phenyl ethylphosphorodithioate, S-[(P-chlorophenylthio)methyl] O,O-dimethyl phosphorodithioate, S-[(p-chlorophenylthio)methyl] O,O-diethylphosphorodiethioate, O,O-dimethyl O-p-nitrophenyl phosphorothioate, O,O-diethyl O-p-nitrophenyl phosphorothioate; and insect hormones and mimics such as:

Cecropia - Juvenile Hormone - I 1-(4'-ethyl)phenoxy-3,7-dimethyl-7,7-epoxy-trans-2-octene 1-(3',4-methylendioxy)phenoxy-3,7-dimethyl-6,7-epoxy-trans-2-nonene Ethyl 3,7,11-trimethyldodeca-2,4-dienoate Isopropyl 11-methoxy-3,7,11-trimethyl-dodeca-2,4-dienoate Capsules of compounds useful for plant disease control provide a route to long term control of disease using compounds generally regarded to have only short term effectiveness. Similarly, herbicides, complementary herbicide antidotes, nematocides, insecticides, rodenticides and soil nutrients can be encapsulated with useful results. Chemicals used for seed treatment are also readily encapsulated by the process of the invention. Other biological products can be encapsulated including: Anthelmintics, lamphrey and slime control agents, algicides, swimming pool chemicals, miticides, acaracides, animal attractants, antiseptics, deodorants, disinfectants, mildewicides, and the like.

The material to be encapsulated utilizing the improved process of the instant invention can be of any type which is water-immiscible. The material need not consist of only one type, but may be a combination of two or more various types of water-immiscible materials. For example, employing an appropriate water-immiscible material, such a combination is an active herbicide and an active insecticide. Also contemplated is a water-immiscible material to be encapsulated which comprises an active ingredient, such as an herbicide and an inactive ingredient such as a solvent or adjuvant. Encapsulation of a solid material can be accomplished by this method by forming a solution of the solid material in an appropriate solvent; thereby, normally solid water-immiscible material can be encapsulated. For example, the insecticide N-(mercaptomethyl) phthalimide S-(O,O-dimethyl phosphorodithioate), m.p. 72° C., can be encapsulated by first dissolving the solid in an appropriate solvent, such as heavy aromatic naphtha solvent.

In addition other representative and especially of importance are the process and capsules comprising as constituents in the organic phase herbicides of the class acetanilide or substituted acetanilide herbicides, particularly the type substituted chloroacetanilide herbicides such as: N-(3'-methoxypropyl-(2))-2-methyl-6-ethyl chloroacetanilide, N-(2'-methoxyethyl)-2,6-dimethyl chloroacetanilide, 2-chloro-2',6'-diethyl-N-(methoxymethyl) acetanilide, 2-chloro-2',6'-diethyl-N-(methylcarbethoxy) acetanilide, 2-chloro-N-isopropylacetanilide, and the like; and 2,4-dichloro and 2, 4, 5-trichloro phenoxy acetic acid, esters and salts thereof.

As important constituents in the organic phase either alone or in combination with complimentary herbicides are the class of agents known as herbicide antidotes can be used with herbicides as mentioned above. Classes of antidotes include N,N-disubstituted haloacetamides, sulfonamides, oxazolidines and thiazolidines, various halogenated esters, halogenated ketones, disulfides, thiuronium salts, a tetrazolium salt and certain imidazolines, certain carbamates, thiocarbamates and dithiocarbamates, cyanomethyl ether of phenyl glyoxylonitrile oxime and substituted pyridyloxy alkanoic acid amides.

What is claimed is:

1. A process for the preparation of encapsulated water-immiscible material within discrete shells of polyurea without external heating which comprises
    (a) providing in an aqueous phase a solution comprising water, a surfactant and a protective colloid;
    (b) adjusting the pH of said aqueous phase to about 2 to about 8;

(c) adding to said pH adjusted aqueous phase a water-immiscible phase comprising the water-immiscible material to be encapsulated, an organic polyisocyanate and a catalytic amount of an organic quaternary salt phase transfer catalyst having the formula $$(R_3R_4R_5R_6M)^+ X^-$$

wherein $R_3$, $R_4$, $R_5$ and $R_6$ are hydrocarbon radicals independently selected from the group consisting of alkyl, alkenyl, aryl, alkaryl aralkyl, and cycloalkyl radicals; M is a member selected from the group consisting of nitrogen, phosphorus, arsenic, antimony, and bismuth; and X is an anion selected from the group consisting of a halide ion and a hydroxyl ion which will dissolve from the cation in an aqueous environment;

(d) dispersing said water-immiscible phase in said aqueous phase to establish droplets of the water-immiscible phase in said aqueous phase;

(e) adjusting the pH of the dispersion to between about pH 8 and about pH 12; whereupon discrete polyurea capsular enclosure forms around the water-immiscible material.

2. The process of claim 1 in which M is nitrogen.

3. The process of claim 1 in which X is a halide.

4. The process of claim 2 in which X is chlorine or bromine.

5. The process of claim 1 in which M is phosphorus.

6. The process of claim 4 in which X is a halide.

7. The process of claim 5 in which X is chlorine or bromine.

8. The process as described in claim 1 in which the organic quaternary salt is selected from the group consisting of tetra-n-butyl phosphonium chloride, tri-n-butyl n-cetyl phosphonium bromide, hexadecyl tributyl phosphonium bromide, benzyl triethyl ammonium chloride, benzyl triethyl ammonium bromide, tricaprylyl methyl ammonium chloride, and dimethyl dicoco ammonium chloride.

9. The process of claim 1 in which said water-immiscible material is a water-immiscible organic material.

10. The process of claim 1 wherein the organic phase contains organic polyisocyanate within the range of about 20 percent to about 75.0 percent by weight.

11. The process of claim 10 wherein said organic polyisocyanate is an aromatic diisocyanate.

12. The process of claim 11 wherein said aromatic diisocyanate is about 80 percent 2,4- and about 20 percent 2,6-isomer of tolylene diisocyanate.

13. The process of claim 10 wherein said organic polyisocyanate is aromatic polyisocyanate.

14. The process of claim 13 wherein said aromatic polyisocyanate is polymethylene polyphenylisocyanate.

15. The process of claim 10 wherein said organic polyisocyanate is an aliphatic diisocyanate.

16. The process of claim 15 wherein said aliphatic diisocyanate is hexamethylene diisocyanate.

17. The process of claim 10 wherein said organic polyisocyanate is a combination of aromatic isocyanate and aliphatic polyisocyanates.

18. The process of claim 17 wherein said aromatic polyisocyanate is polymethylene polyphenylisocyanate and said aliphatic polyisocyanate is hexamethylene diisocyanate.

19. The process of claim 9 for encapsulating water-immiscible organic material wherein the organic phase added to the aqueous phase is a combination of organic polyisocyanates, percent to about 75 percent by weight.

20. The process of claim 19 wherein said combination of organic polyisocyanates consist of polymethylene polyphenylisocyanate and 80 percent 2,4- and 20 percent 2,6-isomers of tolylene diisocyanate.

21. The process of claim 1 wherein said water-immiscible organic material is a thiocarbamate herbicide whereupon said thiocarbamate herbicide is encapsulated within a polyurea capsular enclosure.

22. The process of claim 21 for encapsulating water-immiscible organic material within a polyurea capsule wherein said thiocarbamate herbicide is S-ethyl diisobutyl thiocarbamate.

23. The process of claim 21 for encapsulating a water-immiscible organic material within a polyurea capsule wherein said thiocarbamate herbicide is S-ethyl dipropylthiocarbamate.

24. The process of claim 21 for encapsulating a water-immiscible organic material within a polyurea capsule wherein said thiocarbamate herbicide is S-ethyl hexahydro-1-H-azepine-1-carbothioate.

25. The process of claim 21 for encapsulating a water-immiscible organic material within a polyurea capsule wherein said thiocarbamate herbicide is S-propyl dipropylthiocarbamate.

26. The process of claim 21 for encapsulating a water-immiscible organic material within a polyurea capsule wherein said thiocarbamate herbicide is S-ethyl ethylcyclohexylthiocarbamate.

27. The process of claim 21 for encapsulating a water-immiscible organic material within a polyurea capsule wherein said thiocarbamate herbicide is S-propyl butylethylthiocarbamate.

28. The process of claim 21 for encapsulating a water-immiscible organic material within a polyurea capsule wherein said thiocarbamate herbicide is S-propyl hexahydro-1-H-azepine-1-carbothioate.

29. The process of claim 1 wherein said water-immiscible organic material is an organophosphorus insecticide and whereupon said organophosphorus insecticide is encapsulated within a polyurea capsular enclosure.

30. The process of claim 29 for encapsulating a water-immiscible organic material within a polyurea capsule wherein said organophosphorus insecticide is O-ethyl S-phenyl ethylphosphonodithioate.

31. The process of claim 29 for encapsulating a water-immiscible organic material within a polyurea capsule wherein said organophosphorus insecticide is O,O-dimethyl O-p-nitrophenyl phosphorothioate.

32. The process of claim 29 for encapsulating a water-immiscible organic material within a polyurea capsule wherein said organophosphorus insecticide is O,O-diethyl O-p-nitrophenyl phosphorothioate.

33. The process of claim 29 for encapsulating a water-immiscible organic material within a polyurea capsule wherein said organophosphorus insecticide is S[(p-chlorophenylthio)methyl] O,O-dimethyl phosphorodithioate.

34. The process of claim 29 for encapsulating a water-immiscible organic material within a polyurea capsule wherein said organophosphorus insecticide is S[(p-chlorophenylthio)methyl] O,O-diethyl phosphorodithioate.

35. The process of claim 1 wherein said water-immiscible organic material is an insect hormone mimic whereupon said insect hormone mimic is encapsulated within a polyurea capsular enclosure.

36. The process of claim 35 for encapsulating a water-immiscible organic material within a polyurea capsule wherein said insect hormone mimic is 1-(4'-ethyl)-phenoxy-3,7-dimethyl-6,7-epoxy-trans-2-octene.

37. The process as described in claim 1 used to encapsulate a mixture of an herbicide and a complimentary antidote therefore.

38. The process of claim 37 in which the herbicide is S-ethyl diisobutyl thiocarbamate and the complimentary antidote is N,N-diallyl dichloroacetamide.

39. The process of claim 37 in which the herbicide is S-ethyl dipropylthiocarbamate and the complimentary antidote is N,N-diallyl dichloroacetamide.

40. The process of claim 37 in which the herbicide is S-propyl dipropylthiocarbamate and the complimentary antidote is N,N-diallyl dichloroacetamide.

41. A process for the preparation of encapsulated water-immiscible material within discrete shells of polyurea without external heating which comprises
(a) providing in an aqueous phase a solution comprising water, a surfactant and a protective colloid;
(b) adjusting the pH of said aqueous phase to about 5 to about 10;
(c) adding to said pH adjusted aqueous phase a water-immiscible phase comprising the water-immiscible material to be encapsulated, an organic polyisocyanate and a catalytic amount of an organic quaternary salt phase transfer catalyst having the formula

wherein $R_3$, $R_4$, $R_5$ and $R_6$ are hydrocarbon radicals independently selected from the group consisting of alkyl, alkenyl, aryl, alkaryl, aralkyl and cycloalkyl radicals; M is a member selected from the group consisting of nitrogen, phosphorus, arsenic, antimony and bismuth; and X is an anion selected from the group consisting of a halide ion and a hydroxyl ion which will dissolve from the cation in an aqueous environment;
(d) dispersing said water-immiscible phase in said aqueous phase to establish droplets of the water-immiscible phase in said aqueous phase; whereupon discrete polyurea capsular enclosure forms around the water-immiscible material.

42. The process as described in claim 41 in which the organic quaternary salt is selected from the group consisting of tetra-n-butyl phosphonium chloride, tri-n-butyl n-cetyl phosphonium bromide, hexadecyl tributyl phosphonium bromide, benzyl triethyl ammonium chloride, benzyl triethyl ammonium bromide, tricaprylyl methyl ammonium chloride, and dimethyl dicoco ammonium chloride.

43. The process of claim 41 wherein the organic phase contains organic polyisocyanate within the range of about 20 percent to about 75.0 percent by weight.

44. The process of claim 41 wherein said water-immiscible organic material is a thiocarbamate herbicide whereupon said thiocarbamate herbicide is encapsulated within a polyurea capsular enclosure.

45. The process of claim 41 wherein said water-immiscible organic material is an organophosphorus insecticide and whereupon said organophosphorus insecticide is encapsulated within a polyurea capsular enclosure.

46. The process of claim 41 wherein said water-immiscible organic material is an insect hormone mimic whereupon said insect hormone mimic is encapsulated within a polyurea capsular enclosure.

* * * * *

UNITED STATES PATENT AND TRADEMARK OFFICE
CERTIFICATE OF CORRECTION

PATENT NO. : 4,140,516
DATED : February 20, 1979
INVENTOR(S) : Herbert B. Scher

It is certified that error appears in the above—identified patent and that said Letters Patent are hereby corrected as shown below:

Column 5, line 28 reading "2,2',5.5'-Tetramethyl-4,4'-biphenylene diisocyanate" should read ---2,2'5,5'-Tetramethyl-4,4'-biphenylene diisocyanate---.

Column 6, line 7, the word reading "wall" should read ---will---.

Column 13, Claim 19, the last line reading "polyisocyanate, percent to about 75 percent by weight." should read ---polyisocyanates from about 2.0 percent by weight.---

Signed and Sealed this

Tenth Day of June 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,140,516
DATED : February 20, 1979
INVENTOR(S) : Herbert B. Scher

It is certified that error appears in the above-identified patent and that said Letters Patent are hereby corrected as shown below:

Column 6, line 6, the word reading "wall" should read ---will---.

Signed and Sealed this

Fifth Day of May 1981

[SEAL]

Attest:

RENE D. TEGTMEYER

Attesting Officer    Acting Commissioner of Patents and Trademarks